(12) United States Patent
Hirzel

(10) Patent No.: US 8,460,320 B2
(45) Date of Patent: Jun. 11, 2013

(54) URETHROVESICAL ANASTOMOSIS SUTURING METHOD USING ARTICULATING LAPAROSCOPIC DEVICE

(75) Inventor: Deanna L. Hirzel, Chelsea, MI (US)

(73) Assignee: Terumo Kabushiki Kaisha, Tokyo (JP)

(*) Notice: Subject to any disclaimer, the term of this patent is extended or adjusted under 35 U.S.C. 154(b) by 273 days.

(21) Appl. No.: 13/039,418

(22) Filed: Mar. 3, 2011

(65) Prior Publication Data

US 2012/0226292 A1   Sep. 6, 2012

(51) Int. Cl.
*A61B 17/04* (2006.01)
*A61B 17/12* (2006.01)

(52) U.S. Cl.
USPC ........................................................ 606/144

(58) Field of Classification Search
None
See application file for complete search history.

(56) References Cited

U.S. PATENT DOCUMENTS

2009/0240263 A1   9/2009   Kawai et al.

OTHER PUBLICATIONS

Van Velthoven, et al., Rapid Communication, Technique for Laparoscopic Running Urethrovesical Anastomosis: The Single Knot Method, Urology 61: 699-702, 2003, pp. 699-702.
Marcos P. Freire, et al., Overcoming the Learning Curve for Robotic-Assisted Laparoscopic Radical Prostatectomy, Urol Clin N Am 37 (2010) 37-40, pp. 37-47.
Elise Perer, et al., Robotic Revelation: Laparoscopic Radical Prostatectomy by a Nonlaparoscopic Surgeon, 2003, pp. 693-696.

*Primary Examiner* — Melanie Tyson
(74) *Attorney, Agent, or Firm* — Gael Diane Tisack, Esq.; Darryl Newell; McMillan, Sobanski & Todd

(57) ABSTRACT

A suturing method for anastomosis of live bodies and training bodies joins a duct having perimeter positions defined according to clock hour positions to an opening in a bladder using an articulating laparoscopic device having a gripper at a distal end with open and closed positions for loading a suture needle in either a forehand or backhand direction. The gripper has a yaw motion including left and right positions and a roll motion either clockwise or counterclockwise. The open and closed positions, yaw motion, and roll motion are under manual control of a user through manual controls at a proximal end of the articulating laparoscopic device. The perimeter positions include a 12-o'clock position proximal to the user and a 6-o'clock position distal of the user. The method includes driving a suture at about the 6-o'clock position through the bladder and then the duct wherein the suture needle is loaded forehand, the yaw is in a left position, and the roll is clockwise. Orientations and directions are provided for other suturing positions.

20 Claims, 7 Drawing Sheets

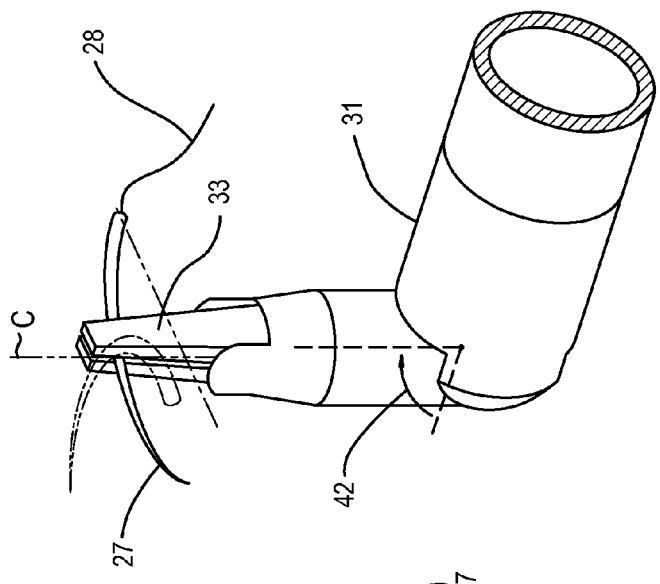
FIG. 4
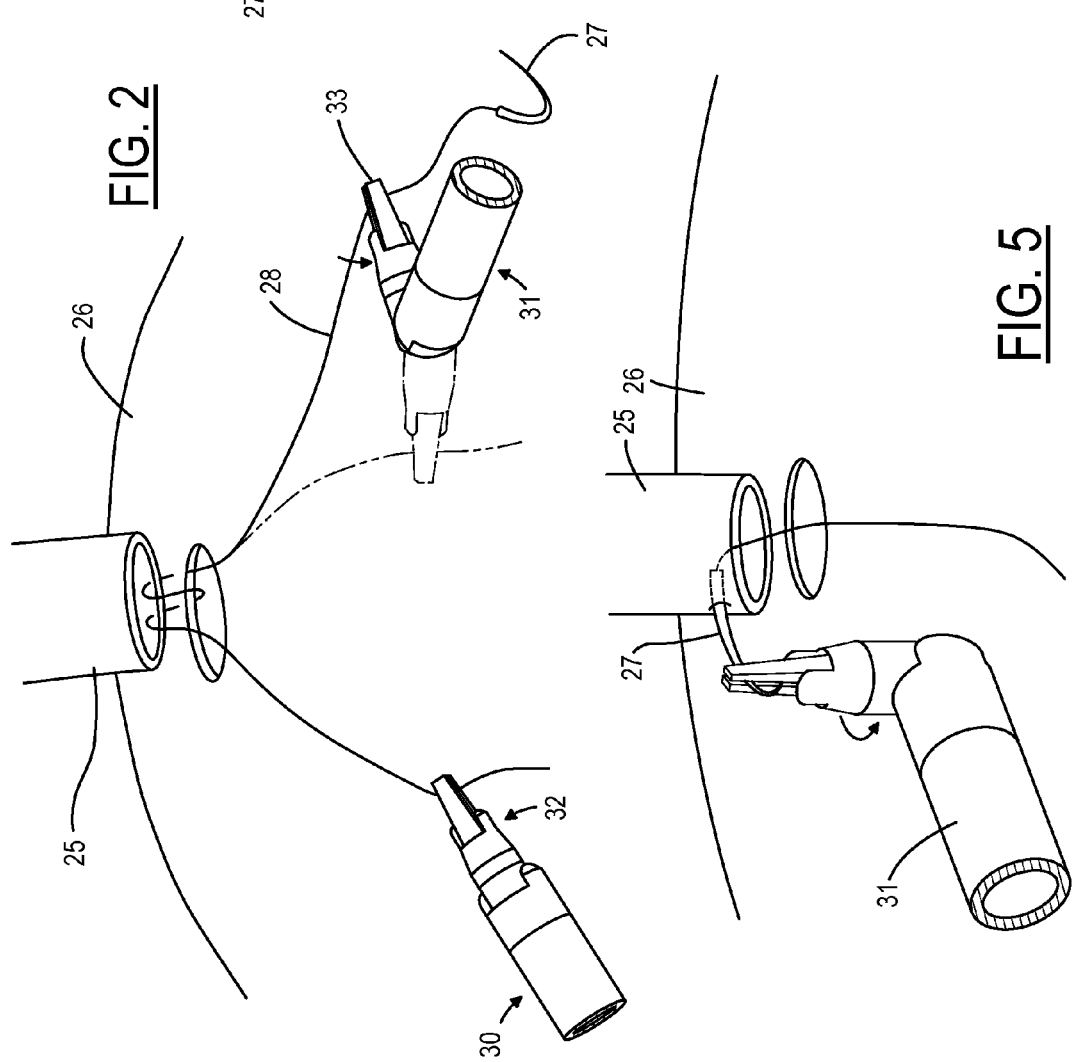
FIG. 2
FIG. 5

URETHROVESICAL ANASTOMOSIS SUTURING METHOD USING ARTICULATING LAPAROSCOPIC DEVICE

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to a method of suturing for use in the training for and performance of certain laparoscopic procedures, and, more specifically, to a suturing method useful for urethrovesical anastomosis.

A prostatectomy is the surgical removal of the prostate gland. During this procedure, a surgical connection known as an anastomosis is performed between the urethra and the bladder neck. Besides this urethrovesical anastomosis, many other surgical procedures also involve making a sutured connection of a tubular structure such as a blood vessel or a portion of the digestive tract.

Laparoscopic techniques are preferentially used in order to achieve improved patient outcomes resulting from minimally invasive procedures. In certain types of endoscopic surgery (e.g., some laparoscopic surgeries), it is customary to form a plurality of incisions in the body surface of the patient, insert trocars (tubular instruments) into the respective incisions as instrument passage ports, and introduce the tip ends of instruments having shafts through the respective trocars and into the body cavity in order to perform a surgical operation on the affected part of the body. Working manipulators (i.e., forceps) such as a gripper for gripping living tissue, scissors, the blade of an electrosurgical knife, etc., may be mounted on the tip ends of the laparoscopic instruments.

Because the working space within the body cavity is small, manipulators passing through the trocars are moved within the cavity using the trocars as fulcrums. Many conventional instruments do not have joints in the working unit on the tip end thereof. Because of the small degree of freedom of movement, the types of endoscopic surgery that can be performed with such instruments are limited to a certain range. Therefore, instruments have been developed having a plurality of joints in a working unit thereof (see, for example, Japanese Laid-Open Patent Publication No. 2002-102248 and U.S. Patent Application Publication 2009/0240263, incorporated herein by reference). Such a manipulator reduces many of the limitations and difficulties posed by conventional forceps instruments.

Manipulators are becoming available with grippers on the tip that articulate with both a yaw motion and a roll motion. The motions may be motor driven. Even with improved manipulators, however, certain laparoscopic procedures remain difficult to perform and train for. A source of difficulty is that the proper placement and motion of the gripper when performing tasks (such as suturing for a urethrovesical anastomosis) involves three-dimensional interpretation and planning on the part of the surgeon who views the surgery via a two-dimensional endoscopic camera. Orientation of the suturing needle, positioning of the joints of the manipulator, and the direction of driving of the various parts of the manipulator all affect whether a successful result is obtained. Therefore, it would be desirable to simplify the procedure for an anastomosis.

SUMMARY OF THE INVENTION

The invention provides an advantageous method for performing a laparoscopic anastomosis with a series of suturing steps that provides predetermined orientations and driving directions according to the various suturing positions.

In one aspect of the invention, a suturing method is provided for anastomosis of live bodies and training bodies wherein a duct having perimeter positions defined according to clock hour positions is joined to an opening in a bladder using an articulating laparoscopic device having a gripper at a distal end with open and closed positions for loading a suture needle in either a forehand or backhand direction. The gripper has a yaw motion including left and right positions and a roll motion either clockwise or counterclockwise. The open and closed positions, yaw motion, and roll motion are under manual control of a user through manual controls at a proximal end of the articulating laparoscopic device. The perimeter positions include a 12-o'clock position proximal to the user, a 6-o'clock position distal of the user, and 3-o'clock and 9-o'clock positions between the 12-o'clock and 6-o'clock positions. The method (adapted for right-handed use) includes driving a suture at about the 6-o'clock position through the bladder and then the duct wherein the suture needle is loaded forehand, the yaw is in a left position, and the roll is clockwise. A suture is driven at a location from about the 7-o'clock position to about the 8-o'clock position through the bladder and then the duct wherein the suture needle is loaded backhand, the yaw is in a right position, and the roll is counterclockwise. A suture is driven at about the 9-o'clock position through the bladder and then the duct wherein the suture needle is loaded backhand, the yaw is in a right position, and the roll is counterclockwise. A suture is driven at a location from about the 4-o'clock position to about the 5-o'clock position through the bladder and then the duct wherein the suture needle is loaded forehand, the yaw is in a left position, and the roll is clockwise. A suture is driven at about the 3-o'clock position through the bladder and then the duct wherein the suture needle is loaded forehand, the yaw is in a right position, and the roll is clockwise. A suture is driven at a location from about the 10-o'clock position to about the 11-o'clock position through the bladder and then the duct wherein the suture needle is loaded backhand, the yaw is in a left position, and the roll is counterclockwise. A suture is driven at a location from about the 1-o'clock position to about the 2-o'clock position through the bladder and then the duct wherein the suture needle is loaded forehand, the yaw is in a right position, and the roll is clockwise. And a suture at about the 12-o'clock position through the bladder and then the duct wherein the suture needle is loaded backhand, the yaw is in a left position, and the roll is counterclockwise.

BRIEF DESCRIPTION OF THE DRAWINGS

FIG. 2 is a partial laparoscopic view during suturing of a bladder and a duct.

FIG. 4 is a perspective view of a gripper while it grips a suturing needle.

FIG. 5 is a perspective view of the rolling of a gripper to pull a suturing needle through the duct.

DETAILED DESCRIPTION OF PREFERRED EMBODIMENTS

Figure 1:
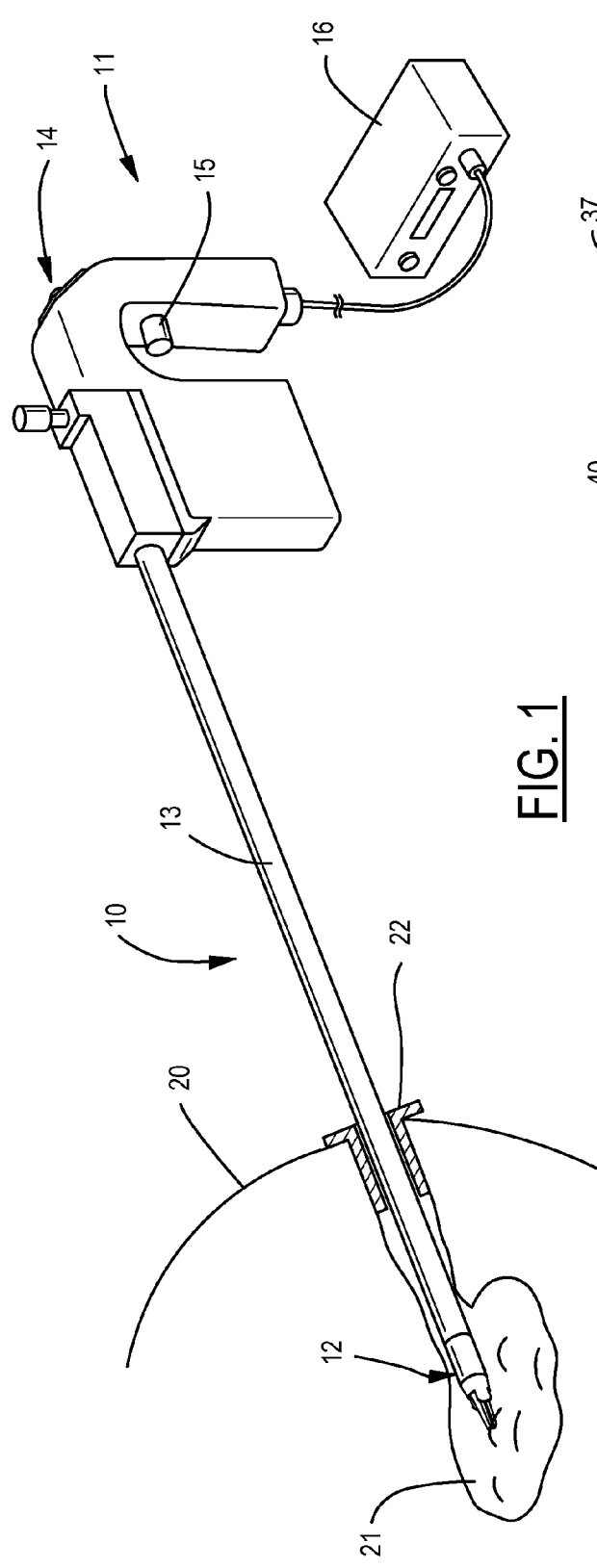
FIG. 1 is a perspective view of a manipulator engaged in laparoscopic surgery.

Referring to FIG. 1, an articulating manipulator 10 has a handle 11 and a working unit 12 joined by a hollow shaft 13. Handle 11 is at the proximal end of manipulator 10 and has manual controls such as buttons 14 and 15 for controlling the operation of a gripper on working unit 12. A controller 16 is connected to handle 11 for providing power to various motors in handle 11 (not shown). In an alternative embodiment, manipulator 10 could operate without motors for power assist by appropriate manual controls and linkages as known in the art.

A body 20 is shown undergoing a laparoscopic procedure in a cavity 21 accessible through a trocar 22. A typical surgery requires two or more such manipulators and entry sites with trocars. By providing an articulating working unit 12 at the distal tip, the size of cavity 21 required for a particular procedure may be reduced and the range of actual actions that can be achieved within cavity 21 is increased.

As shown in FIG. 2, a procedure may include an anastomosis wherein a duct 25 such as a urethra is joined with another anatomical structure such as a bladder 26. Suturing for the anastomosis is typically performed using a suturing needle 27 joined to suturing thread 28 which are manipulated by articulating manipulators 30 and 31. Specifically, grippers 32 and 33 manipulate needle 27 and thread 28 under manual control of a surgeon. An endoscopic camera (not shown) entering the cavity from a third incision provides the surgeon with a view into the cavity during the anastomosis. Due to the two dimensional nature of the camera view and the complexity of the various motions to be executed by the articulating grippers, the anastomosis procedure becomes difficult.

Figure 3:
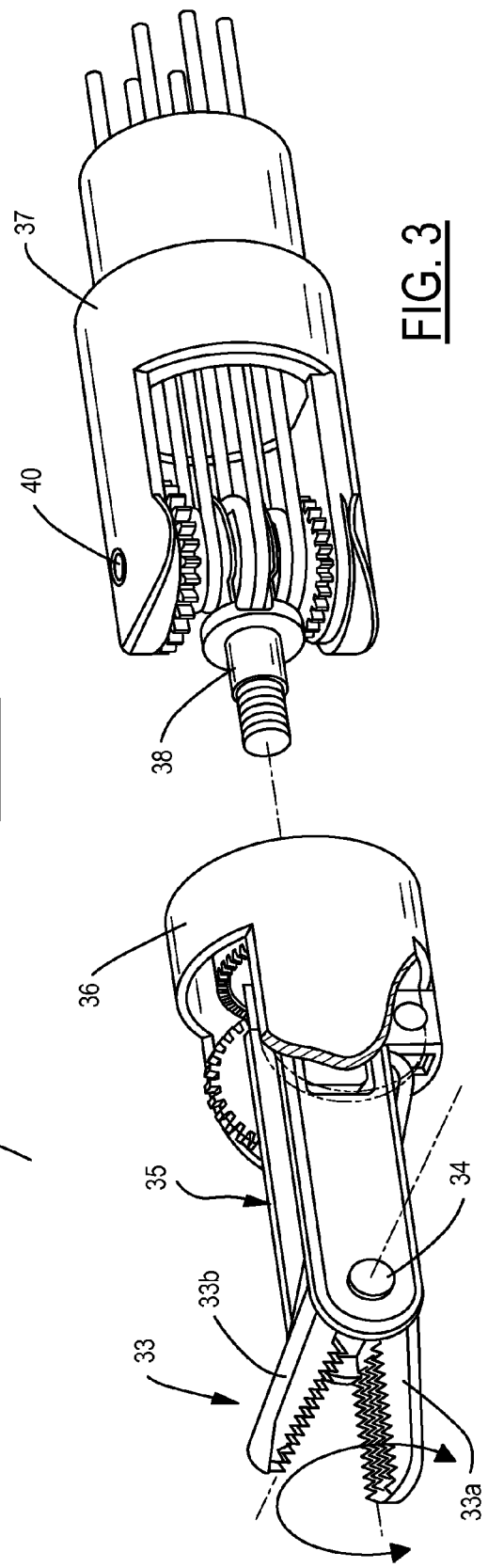
FIG. 3 is a partially exploded view of a manipulator tip.

FIG. 3 shows an exploded view of one example of a distal tip of the manipulator for achieving the various articulations. Gripper 33 has a lower jaw 33a and an upper jaw 33b connected by a pivot pin 34 to a frame 35. A partially shown cover 36 provides a housing for frame 35 which is joined to various linkages in a second cover 37 by a main shaft 38. Main shaft 38 is coupled to a transverse shaft 40 mounted in cover 37. Gears and cables are also provided for transmitting motion to gripper 33 comprised of an opening/closing motion, a yaw or tilting motion, and a rolling motion.

As shown in FIG. 4, a gripper 33 may grasp suturing needle 27 at any particular yaw angle 42 and execute a roll motion around an axis C from a position shown in phantom lines to another position shown in solid lines. It will be understood that passing suture 27 through a duct 25 as shown in FIG. 5, typically involves gripping suturing needle 27 in one gripper to initiate the suture, releasing the suture after passing part way through duct 25, and then gripping suturing needle on the portion having already passed through duct 25 with the other or the same gripper in order to finish the driving of suturing needle 27 through duct 25. Passing suturing needle 27 through corresponding portions of bladder 26 are performed in a similar manner.

In the present invention, all bladder sutures are driven from outside to inside while all urethra sutures are driven from inside to outside. The suturing needle must always be grasped in the jaws of the gripper at substantially a 90° angle to the gripper tip in order to achieve a precise exit point for the driving operation.

Figure 6:
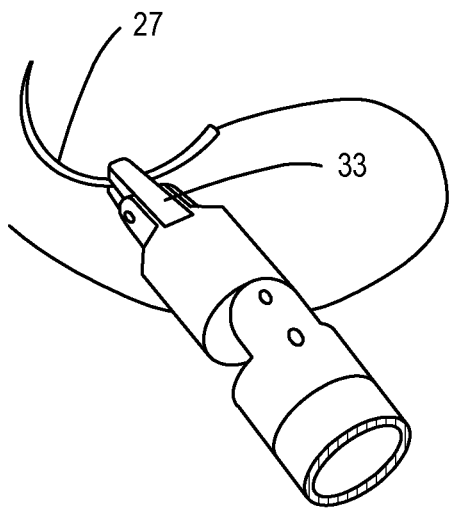
FIG. 6 shows a suturing needle loaded in the forehand direction in a gripper.
Figure 7:
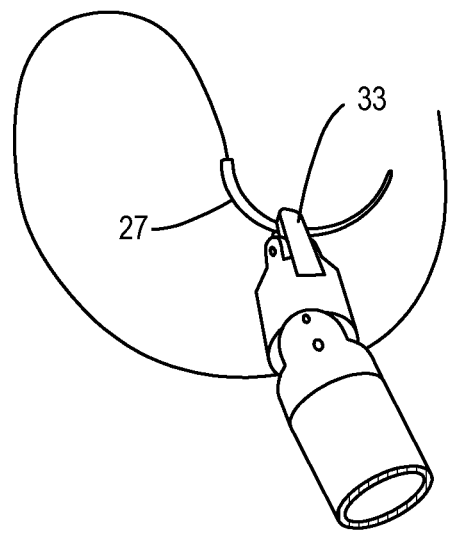
FIG. 7 shows a suturing needle loaded in the backhand direction in a gripper.
Figure 8:
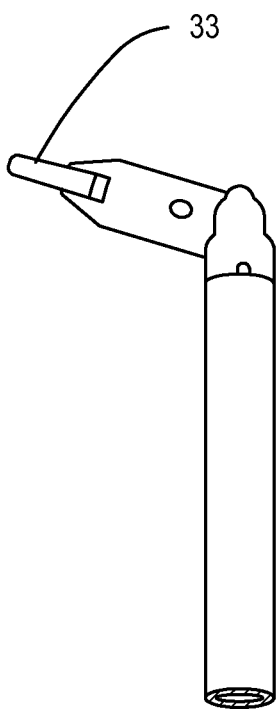
FIG. 8 shows a gripper yawed to the left position.
Figure 9:
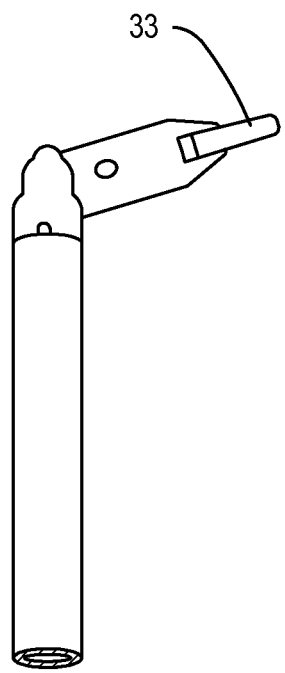
FIG. 9 shows a gripper yawed to the right position.
Figure 10:
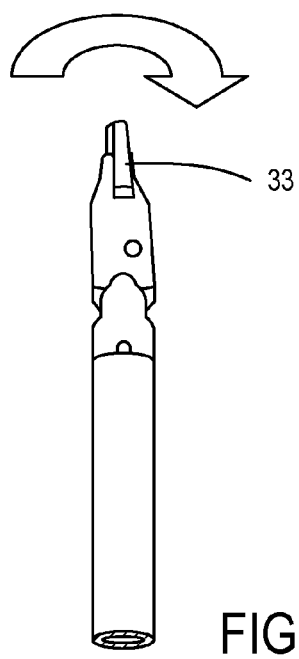
FIG. 10 shows a clockwise roll direction of the gripper.
Figure 11:
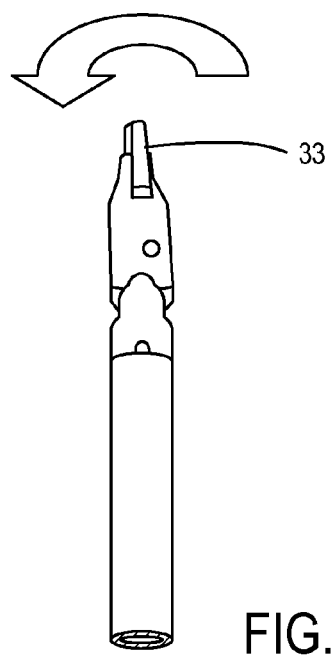
FIG. 11 shows a counterclockwise roll direction of the gripper.

For performing the various suturing steps, the present invention defines predetermined orientations of the gripper and needle according to the views as seen by the surgeon during the suturing procedure. FIG. 6 shows suturing needle 27 loaded in gripper 33 in what is referred to as a forehand or forward direction. In the forehand position, the tip of suturing needle 27 advances when moved in a clockwise direction. FIG. 7 shows the suturing needle loaded in a backhand direction wherein the tip of suturing needle 27 advances when rotated counterclockwise. FIGS. 8 and 9 show tip 33 being yawed in a left and right direction, respectively. FIGS. 10 and 11 show the rolling motion of tip 33 in a clockwise and counterclockwise direction, respectively.

Figure 12:
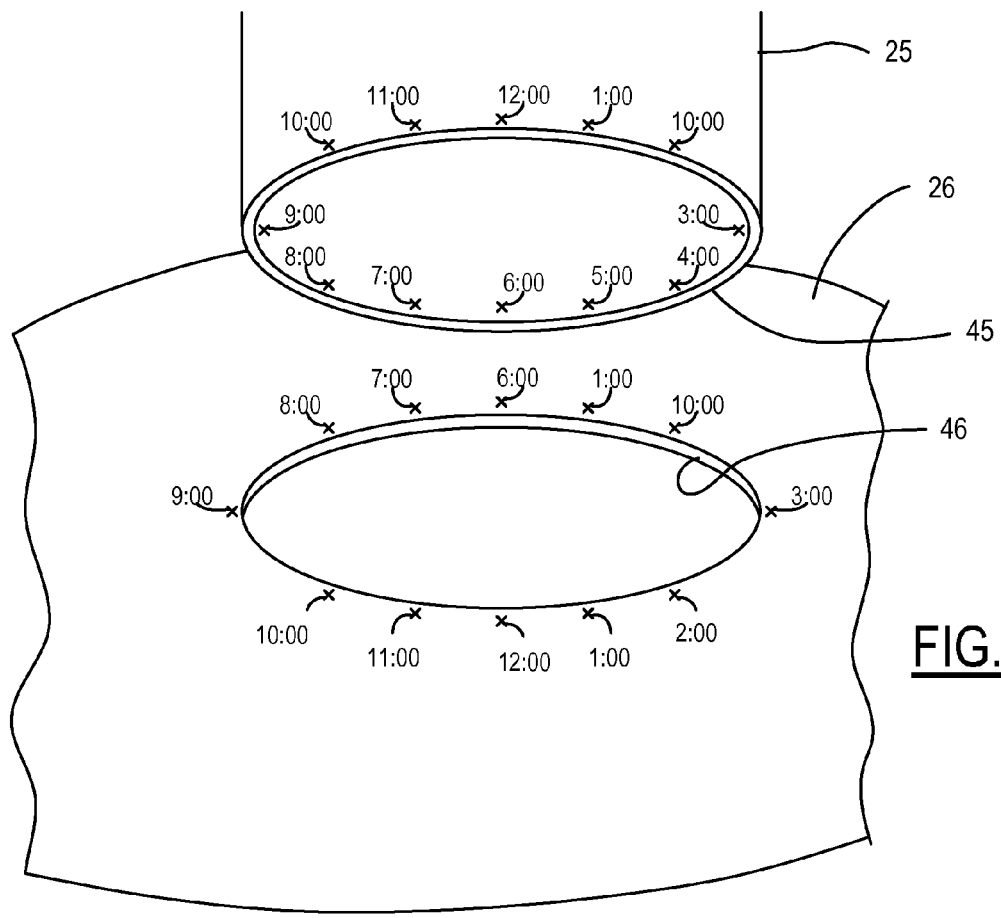
FIG. 12 is a perspective view showing clock hour positions on a bladder and duct that are to be joined.

Anatomical locations of the duct 25 and bladder 26 for attaching an end 45 of duct 25 to the rim of an opening 46 such as a neck of bladder 26 are shown as clock hour positions in FIG. 12. The distal portions (as seen by the surgeon in the endoscopic camera) are designated as the 6-o'clock position since they correspond to the bottom of a typical clock face. The proximal sides are designated as the 12-o'clock positions. On edge 45 of duct 25, the 3-o'clock position is given to the right and the 9-o'clock position is given at the left sides. Correspondingly, the 3-o'clock and 9-o'clock positions on bladder 26 are given to the right and left, respectively. The intermediate clock hour designations as shown may or may not correspond to actual locations for receiving a suture. The present invention defines particular combinations of suture loading, tip yaw, and tip roll directions according to sutures being driven at the cardinal directions (i.e., 12-o'clock, 3-o'clock, 6-o'clock, and 9-o'clock) and for particular ranges between those positions. The directions of the corresponding operations according to the clock hour position of any particular single suture when performing the method as adapted for a right-handed person are shown in the following table.

| Position | Structure | Load Suture | Yaw | Roll |
|---|---|---|---|---|
| 6:00 | Bladder | Forehand | Left | Clockwise |
|  | Urethra | Forehand | Left | Clockwise |
| 7:00-8:00 | Bladder | Backhand | Right | Counterclockwise |
|  | Urethra | Backhand | Right | Counterclockwise |

-continued

| Position | Structure | Load Suture | Yaw | Roll |
|---|---|---|---|---|
| 9:00 | Bladder | Backhand | Right | Counterclockwise |
| | Urethra | Backhand | Right | Counterclockwise |
| 4:00-5:00 | Bladder | Forehand | Left | Clockwise |
| | Urethra | Forehand | Left | Clockwise |
| 3:00 | Bladder | Forehand | Right | Clockwise |
| | Urethra | Forehand | Right | Clockwise |
| 10:00-11:00 | Bladder | Backhand | Left | Counterclockwise |
| | Urethra | Backhand | Left | Counterclockwise |
| 1:00-2:00 | Bladder | Forehand | Right | Clockwise |
| | Urethra | Forehand | Right | Clockwise |
| 12:00 | Bladder | Backhand | Left | Counterclockwise |
| | Urethra | Backhand | Left | Counterclockwise |

The present invention may employ either a continuous, running suture or an interrupted suture (i.e., wherein one or more individual sutures are separately tied off). When loading the suture needle onto the gripper, the plane of the curved needle should be oriented substantially perpendicularly to the longitudinal axis of the gripper. A convenient manner for loading the suture needle is to stabilize the suture in one gripper and then to approach it in a parallel manner with the other gripper (i.e., both grippers being oriented with a straight yaw) in order to grasp the needle at the appropriate location. Preferably, aligning the gripper and needle for performing the step of driving the needle into the duct or bladder includes counter-rotating the gripper with respect to the direction of the subsequent roll direction for driving the needle. Alternatively, the gripper may be rolled in the counter rotation prior to loading the suture needle depending on the surgeon's preference.

After loading of the suture needle into the gripper, the longitudinal axis of the tip of the gripper is aligned substantially perpendicularly to a desired point of entry using the yaw motion. The yaw motion may be in a left or right direction between about zero and ninety degrees. Thus, as provided herein, a left or right direction as defined in the above table may include a nearly straight condition of the gripper depending on various factors such as the laparoscopic entry point.

After a driving step wherein the aligned suture needle is driven in a clockwise or counterclockwise roll direction and penetrates through the corresponding structure, the second gripper may be used to unload the suture needle from the initial gripper and to load the suture needle back into the first gripper for a next driving step. Alternatively, both phases of the needle penetration may be performed with the same gripper while the other is holding a portion of the anatomy in a desired position.

An anastomosis may be performed using any number of individual sutures according to the preference of the surgeon. The above table shows eight different types of suturing steps performed according to the particular region where a suture is being made. Thus, more or less than eight separate sutures may be employed. When a suture is made within a range of about one hour centered on the 6-o'clock, 9-o'clock, 3-o'clock, or 12-o'clock positions, the corresponding details given in the above table are employed. Other specific orientations are employed according to ranges between these cardinal clock positions. By knowing the prescribed suture loading position and yaw and roll directions, the surgeon is relieved of the burden of excessive mental manipulations to organize the ongoing suturing process.

Figure 13:
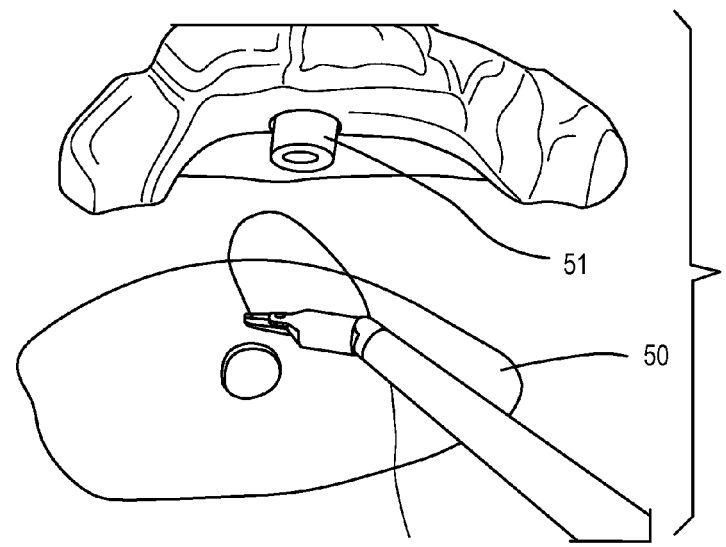
FIG. 13 is a perspective view showing passage of the suturing needle through the bladder during an initial suture of the bladder at the 6-o'clock position.

A typical anastomosis will begin with a suture entered at the distal or 6-o'clock position. At each position, a suture is first penetrated through the bladder and then through the duct at that position. Each driving step is comprised of an outside to inside suturing of the bladder followed by an inside to outside suturing of the duct. FIG. 13 illustrates this first suture with the suture needle having been driven through the bladder at the 6-o'clock position. FIGS. 13-20 illustrate a bladder 50 and a duct 51, which represent either actual organs or a training model which may be constructed from foam rubber, for example.

Figure 14:
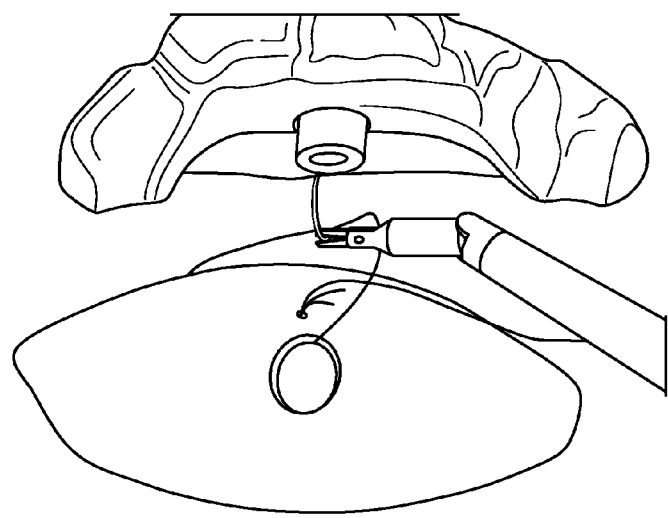
FIG. 14 is a perspective view showing the aligning of the suturing needle in preparation for passage of the suturing needle through the duct for an initial suture of the duct at the 6-o'clock position.

After the initial suture through the bladder at the 6-o'clock position, the suturing thread is advanced to a tied-off position as shown in FIG. 14, and the needle is loaded into the gripper for performing a drive operation through the duct at the 6-o'clock position. As shown in the table, to complete the suture at the 6-o'clock position, the needle is driven clockwise from the inside to the outside of the duct. In both FIGS. 13 and 14, the suture is loaded in the forehand direction, yaw is to the left, and the roll drive is performed in the clockwise direction as specified in the above table.

Depending on surgeon preference and on whether interrupted or continuous sutures are being made, the number of sutures placed and the order in which they are made may vary. For example, sutures from the 9-o'clock through 3-o'clock positions (i.e., those on the distal side of the anastomosis, away from the user) may be performed first. Alternatively, sutures may begin at the 6-o'clock position and run up one side until at or near the 12-o'clock position and then returning to the distal portion of the remaining side and back up to at or near the 12-o'clock position. The following Figures correspond to some of the sutures made according to this second alternative.

Figure 15:
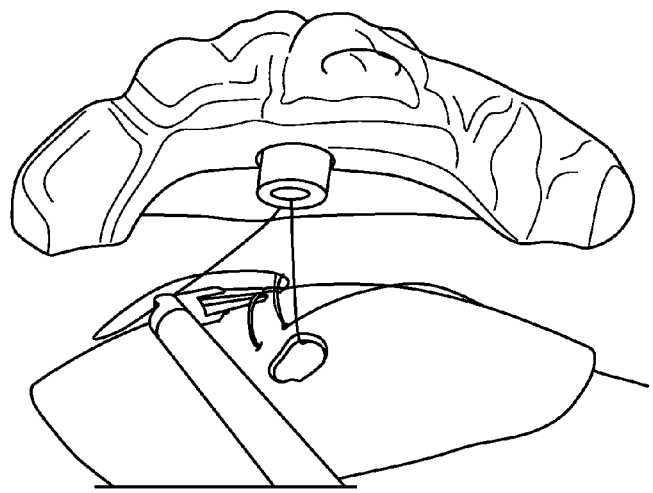
FIGS. 15 and 16 show a second suture of the bladder at a location from about the 7-o'clock position to about the 8-o'clock position.
Figure 16:
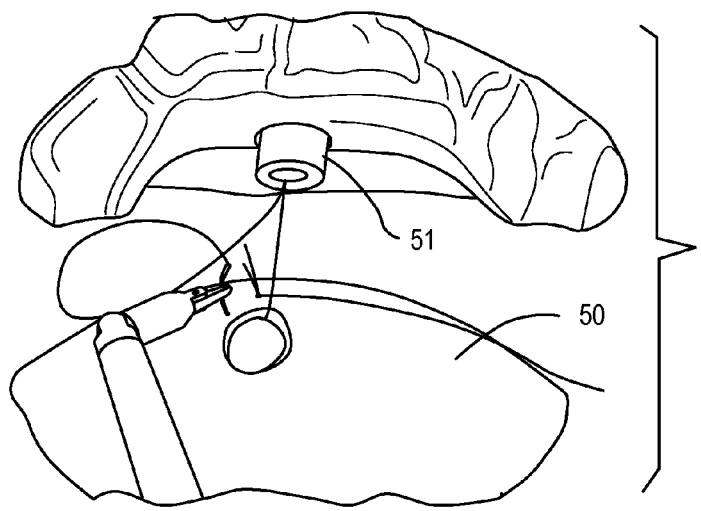

As shown in FIG. 15, the second suture may be driven at a location from about the 7-o'clock position to about the 8-o'clock position. The needle is loaded backhand in the gripper, and yaw is made to the right position. Roll is performed in the counterclockwise direction to drive the suture from the outside to the inside of the bladder. FIG. 16 shows the partial performance of the roll maneuver with the suture needle driven partially through the bladder (i.e., immediately after the situation shown in FIG. 15).

Figure 17:
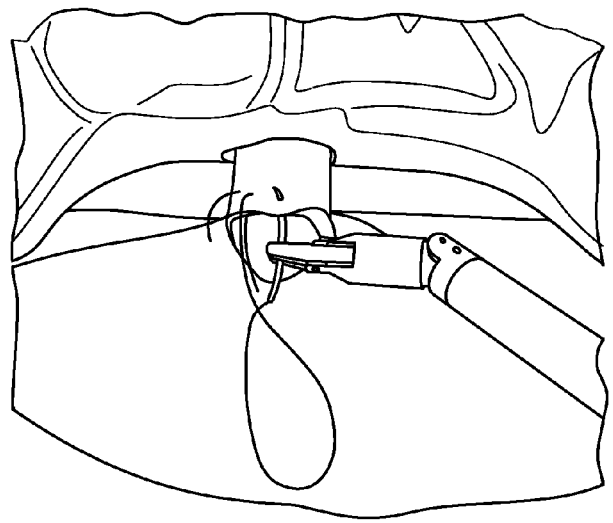
FIG. 17 shows a suture of the duct at the 12-o'clock position.

A continuous suturing then proceeds along the left-hand side of the anastomosis through the 9-o'clock position up to the 12-o'clock position. FIG. 17 shows a urethral suture being made at the 12-o'clock position after the 12-o'clock bladder suture has been made. Thus, the suture needle has been loaded backhand, yaw is toward the left, and the roll function rotates the gripper in the counterclockwise direction in order to drive the suture needle through the urethra.

Figure 18:
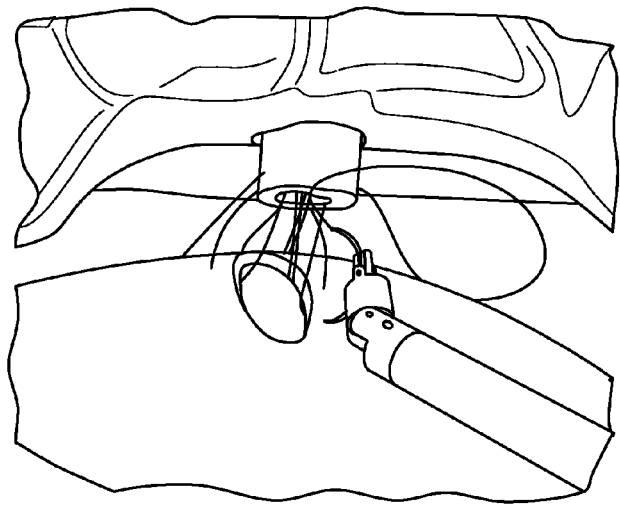
FIG. 18 shows a suture of the bladder at the 3-o'clock position.
Figure 19:
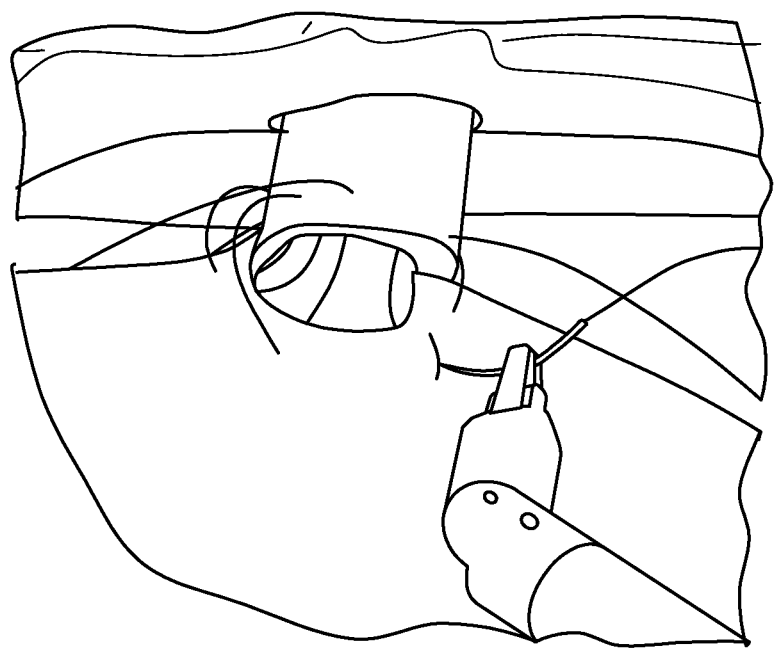
FIG. 19 shows a suture of the bladder at a location from about the 1-o'clock position to about the 2-o'clock position.
Figure 20:
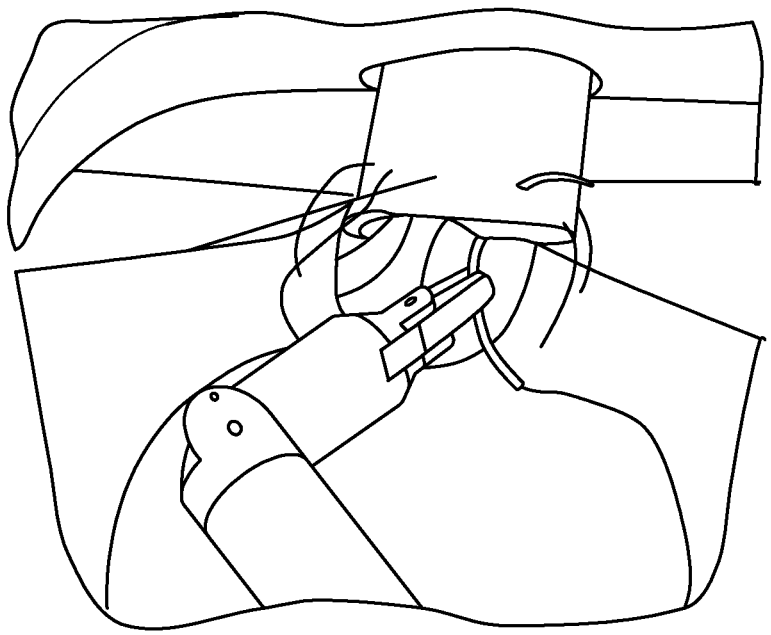
FIG. 20 shows a suture of the duct at a location from about the 1-o'clock position to about the 2-o'clock position.

With the suture needle now on the outside of the duct and bladder following the 12-o'clock urethral suture in FIG. 17, suturing continues in this embodiment at a location from about the 4-o'clock position to about the 5-o'clock position with the suture needle loaded forehand, the yaw in a left position, and the roll clockwise. Then FIG. 18 shows driving a suture at about the 3-o'clock position through the bladder with the suture needle loaded forehand, yaw in a right position, and roll clockwise. Similarly, FIGS. 19 and 20 illustrate driving a suture at a location from about the 1-o'clock position to about the 2-o'clock position through the bladder (FIG. 19) and then the duct (FIG. 20) wherein the suture needle is loaded forehand, the yaw is in a right position, and the roll is clockwise.

Tying off the sutures at the end of a continuous, running suture or after each suturing stitch using an interrupted technique may be performed as known in the art.

In the above explanation, the invention is demonstrated from the perspective of a right-handed user. For a left-handed procedure, the values for loading the suture, the yaw, and the roll would preferably correspond to the directions in the following table.

| Position | Structure | Load Suture | Yaw | Roll |
|---|---|---|---|---|
| 6:00 | Bladder | Forehand | Right | Counterclockwise |
|  | Urethra | Forehand | Right | Counterclockwise |
| 7:00-8:00 | Bladder | Forehand | Right | Counterclockwise |
|  | Urethra | Forehand | Right | Counterclockwise |
| 9:00 | Bladder | Forehand | Left | Counterclockwise |
|  | Urethra | Forehand | Left | Counterclockwise |
| 4:00-5:00 | Bladder | Backhand | Left | Clockwise |
|  | Urethra | Backhand | Left | Clockwise |
| 3:00 | Bladder | Backhand | Left | Clockwise |
|  | Urethra | Backhand | Left | Clockwise |
| 10:00-11:00 | Bladder | Forehand | Left | Counterclockwise |
|  | Urethra | Forehand | Left | Counterclockwise |
| 1:00-2:00 | Bladder | Backhand | Right | Clockwise |
|  | Urethra | Backhand | Right | Clockwise |
| 12:00 | Bladder | Backhand | Right | Counterclockwise |
|  | Urethra | Backhand | Right | Counterclockwise |

The foregoing method demonstrates a standardized method to perform a urethral vesicle anastomosis that is advantageously used by a surgeon during a surgical procedure and also for use as a training method. The surgical procedure and use of the instruments is less cumbersome and frustrating while operating in a small/confined space. The three dimensional relationships encountered by the surgeon are automatically resolved by the standardized steps and orientations.

What is claimed is:

1. A suturing method for anastomosis of live bodies and training bodies wherein a duct having perimeter positions defined according to clock hour positions is joined to an opening in a bladder using an articulating laparoscopic device having a gripper at a distal end with open and closed positions for loading a suture needle in either a forehand or backhand direction, wherein the gripper has a yaw motion including left and right positions and a roll motion either clockwise or counterclockwise, wherein the open and closed positions, yaw motion, and roll motion are under manual control of a user through manual controls at a proximal end of the articulating laparoscopic device, wherein the perimeter positions include a 12-o'clock position proximal to the user, a 6-o'clock position distal of the user, and 3-o'clock and 9-o'clock positions between the 12-o'clock and 6-o'clock positions, the method comprising the steps of:

driving a suture at about the 6-o'clock position through the bladder and then the duct wherein the suture needle is loaded forehand, the yaw is in a left position, and the roll is clockwise;

driving a suture at a location from about a 7-o'clock position to about an 8-o'clock position through the bladder and then the duct wherein the suture needle is loaded backhand, the yaw is in a right position, and the roll is counterclockwise;

driving a suture at about the 9-o'clock position through the bladder and then the duct wherein the suture needle is loaded backhand, the yaw is in a right position, and the roll is counterclockwise;

driving a suture at a location from about a 4-o'clock position to about a 5-o'clock position through the bladder and then the duct wherein the suture needle is loaded forehand, the yaw is in a left position, and the roll is clockwise;

driving a suture at about the 3-o'clock position through the bladder and then the duct wherein the suture needle is loaded forehand, the yaw is in a right position, and the roll is clockwise;

driving a suture at a location from about a 10-o'clock position to about an 11-o'clock position through the bladder and then the duct wherein the suture needle is loaded backhand, the yaw is in a left position, and the roll is counterclockwise;

driving a suture at a location from about a 1-o'clock position to about a 2-o'clock position through the bladder and then the duct wherein the suture needle is loaded forehand, the yaw is in a right position, and the roll is clockwise; and driving a suture at about the 12-o'clock position through the bladder and then the duct wherein the suture needle is loaded backhand, the yaw is in a left position, and the roll is counterclockwise.

2. The method of claim 1 wherein each driving step is comprised of an outside-to-inside suturing of the bladder followed by an inside-to-outside suturing of the duct.

3. The method of claim 1 wherein a second laparoscopic device having a second gripper is used to finish the suturing of the bladder and unload the suture needle from the gripper and to reload the suture needle in the gripper for the suturing of the duct.

4. The method of claim 1 wherein a second laparoscopic device having a second gripper is used to unload the suture needle from the gripper after a driving step and to load the suture needle in the gripper for a next driving step.

5. The method of claim 1 wherein each suture driven with yaw in the left position is comprised of a yaw between about 0° and about 90° to the left.

6. The method of claim 1 wherein each suture driven with yaw in the right position is comprised of a yaw between about 0° and about 90° to the right.

7. The method of claim 1 wherein each driving step includes moving the gripper in a counter-rotation of the respective roll prior to driving the suture.

8. The method of claim 1 wherein each driving step includes moving the gripper in a counter-rotation of the respective roll prior to loading the suture needle.

9. The method of claim 1 wherein a continuous suture is driven by the driving steps.

10. The method of claim 1 wherein an interrupted suture is driven by at least one of the driving steps.

11. The method of claim 1 wherein the anastomosis is a urethrovesical anastomosis wherein the duct is a urethra or a model of a urethra and wherein the bladder is a urinary bladder or a model of a urinary bladder.

12. The method of claim 1 wherein each driving step includes loading the suture needle substantially perpendicularly to a longitudinal axis of the gripper.

13. The method of claim 12 wherein each driving step includes aligning a tip of the gripper substantially perpendicularly to a desired point of entry using the yaw motion.

14. A method of training a user to use an articulating laparoscopic device having a gripper at a distal end with open and closed positions for loading a suture needle in either a forehand or backhand direction, wherein the gripper has a yaw motion including left and right positions and a roll motion either clockwise or counterclockwise, wherein the open and closed positions, yaw motion, and roll motion are under manual control of a user through manual controls at a proximal end of the articulating laparoscopic device, wherein the training simulates a urethrovesical anastomosis of a training body with a duct having perimeter positions defined according to clock hour positions which is joined to an opening in a bladder, wherein the perimeter positions include a 12-o'clock position proximal to the user, a 6-o'clock position distal of the user, and 3-o'clock and 9-o'clock positions between the 12-o'clock and 6-o'clock positions, the method comprising the steps of:

driving a suture at about the 6-o'clock position through the bladder and then the duct wherein the suture needle is loaded forehand, the yaw is in a left position, and the roll is clockwise;

driving a suture at a location from about a 7-o'clock position to about an 8-o'clock position through the bladder and then the duct wherein the suture needle is loaded backhand, the yaw is in a right position, and the roll is counterclockwise;

driving a suture at about the 9-o'clock position through the bladder and then the duct wherein the suture needle is loaded backhand, the yaw is in a right position, and the roll is counterclockwise;

driving a suture at a location from about a 4-o'clock position to about a 5-o'clock position through the bladder and then the duct wherein the suture needle is loaded forehand, the yaw is in a left position, and the roll is clockwise;

driving a suture at about the 3-o'clock position through the bladder and then the duct wherein the suture needle is loaded forehand, the yaw is in a right position, and the roll is clockwise;

driving a suture at a location from about a 10-o'clock position to about an 11-o'clock position through the bladder and then the duct wherein the suture needle is loaded backhand, the yaw is in a left position, and the roll is counterclockwise;

driving a suture at a location from about a 1-o'clock position to about a 2-o'clock position through the bladder and then the duct wherein the suture needle is loaded forehand, the yaw is in a right position, and the roll is clockwise; and driving a suture at about the 12-o'clock position through the bladder and then the duct wherein the suture needle is loaded backhand, the yaw is in a left position, and the roll is counterclockwise.

15. A left-handed suturing method for anastomosis of live bodies and training bodies wherein a duct having perimeter positions defined according to clock hour positions is joined to an opening in a bladder using an articulating laparoscopic device having a gripper at a distal end with open and closed positions for loading a suture needle in either a forehand or backhand direction, wherein the gripper has a yaw motion including left and right positions and a roll motion either clockwise or counterclockwise, wherein the open and closed positions, yaw motion, and roll motion are under manual control of a user through manual controls at a proximal end of the articulating laparoscopic device, wherein the perimeter positions include a 12-o'clock position proximal to the user, a 6-o'clock position distal of the user, and 3-o'clock and 9-o'clock positions between the 12-o'clock and 6-o'clock positions, the method comprising the steps of:

driving a suture at about the 6-o'clock position through the bladder and then the duct wherein the suture needle is loaded forehand, the yaw is in a right position, and the roll is counterclockwise;

driving a suture at a location from about a 7-o'clock position to about an 8-o'clock position through the bladder and then the duct wherein the suture needle is loaded forehand, the yaw is in a right position, and the roll is counterclockwise;

driving a suture at about the 9-o'clock position through the bladder and then the duct wherein the suture needle is loaded forehand, the yaw is in a left position, and the roll is counterclockwise;

driving a suture at a location from about a 4-o'clock position to about a 5-o'clock position through the bladder and then the duct wherein the suture needle is loaded backhand, the yaw is in a left position, and the roll is clockwise;

driving a suture at about the 3-o'clock position through the bladder and then the duct wherein the suture needle is loaded backhand, the yaw is in a left position, and the roll is clockwise;

driving a suture at a location from about a 10-o'clock position to about an 11-o'clock position through the bladder and then the duct wherein the suture needle is loaded backhand, the yaw is in a left position, and the roll is counterclockwise;

driving a suture at a location from about a 1-o'clock position to about a 2-o'clock position through the bladder and then the duct wherein the suture needle is loaded backhand, the yaw is in a right position, and the roll is clockwise; and driving a suture at about the 12-o'clock position through the bladder and then the duct wherein the suture needle is loaded backhand, the yaw is in a right position, and the roll is counterclockwise.

16. The method of claim 15 wherein each driving step is comprised of an outside-to-inside suturing of the bladder followed by an inside-to-outside suturing of the duct.

17. The method of claim 15 wherein a second laparoscopic device having a second gripper is used to finish the suturing of the bladder and unload the suture needle from the gripper and to reload the suture needle in the gripper for the suturing of the duct.

18. The method of claim 15 wherein a second laparoscopic device having a second gripper is used to unload the suture needle from the gripper after a driving step and to load the suture needle in the gripper for a next driving step.

19. The method of claim 15 wherein each suture driven with yaw in the left position is comprised of a yaw between about 0° and about 90° to the left.

20. The method of claim 15 wherein each suture driven with yaw in the right position is comprised of a yaw between about 0° and about 90° to the right.

\* \* \* \* \*